(12) United States Patent
Apell et al.

(10) Patent No.: US 9,846,766 B2
(45) Date of Patent: Dec. 19, 2017

(54) METHOD FOR MONITORING THE FILLING OF A MEDICATION DISPENSER, AND MEDICATION DISPENSER

(71) Applicant: EVONDOS OY, Salo (FI)

(72) Inventors: Mika Apell, Turku (FI); Jyrki Niinistö, Halikko (FI)

(73) Assignee: EVONDOS OY, Salo (FI)

( * ) Notice: Subject to any disclaimer, the term of this patent is extended or adjusted under 35 U.S.C. 154(b) by 161 days.

(21) Appl. No.: 13/932,298

(22) Filed: Jul. 1, 2013

(65) Prior Publication Data
US 2014/0005826 A1 Jan. 2, 2014

(30) Foreign Application Priority Data
Jun. 29, 2012 (EP) .................................... 12174381

(51) Int. Cl.
| | | |
|---|---|---|
| G06F 19/00 | (2011.01) | |
| G07F 9/02 | (2006.01) | |
| G07F 17/00 | (2006.01) | |
| G07F 11/68 | (2006.01) | |
| A61J 7/00 | (2006.01) | |
| A61J 1/03 | (2006.01) | |

(52) U.S. Cl.
CPC ........ *G06F 19/3462* (2013.01); *A61J 7/0076* (2013.01); *G07F 9/026* (2013.01); *G07F 11/68* (2013.01); *G07F 17/0092* (2013.01); *A61J 1/035* (2013.01); *A61J 2205/10* (2013.01); *A61J 2205/30* (2013.01)

(58) Field of Classification Search
CPC ...... G07F 11/12; G07F 9/026; G06F 19/3462; A61J 7/0076; A61J 1/035; A61J 2205/30

USPC ................................ 700/236, 240, 242–244
See application file for complete search history.

(56) References Cited

U.S. PATENT DOCUMENTS

| | | | |
|---|---|---|---|
| 4,971,221 A | | 11/1990 | Urquhart et al. |
| 5,097,982 A | | 3/1992 | Kedem et al. |
| 5,102,008 A | * | 4/1992 | Kaufman ............... A61J 7/0481 221/25 |
| 5,230,441 A | * | 7/1993 | Kaufman ............... A61J 7/0481 221/197 |
| 5,335,816 A | * | 8/1994 | Kaufman ............... A61J 7/0481 221/124 |
| 5,805,051 A | | 9/1998 | Herrmann et al. |
| 5,945,651 A | * | 8/1999 | Chorosinski ......... G06Q 10/087 235/375 |

(Continued)

FOREIGN PATENT DOCUMENTS

| | | |
|---|---|---|
| EP | 2026298 A1 | 2/2009 |
| EP | 2 457 550 A1 | 5/2012 |

(Continued)

*Primary Examiner* — Michael K Collins
(74) *Attorney, Agent, or Firm* — Buchanan Ingersoll & Rooney PC

(57) ABSTRACT

A method for monitoring the filling of a medication dispenser that comprises a first and a second container for receiving a strip of medication packages. In the method a taking time of the first medication package of the second strip inserted into the second container is compared with a taking time of the last medication package of the first strip inserted into the first container, in order to determine if the delivery of medication packages can be continued after the first strip with the second strip. The invention also relates to a medication dispenser.

18 Claims, 2 Drawing Sheets

(56) References Cited

U.S. PATENT DOCUMENTS

| | | | |
|---|---|---|---|
| 6,394,306 B1* | 5/2002 | Pawlo | A61J 7/0409 221/15 |
| 6,529,446 B1 | 3/2003 | De la Huerga | |
| 6,601,729 B1* | 8/2003 | Papp | A61J 7/0084 206/528 |
| 7,264,136 B2* | 9/2007 | Willoughby | B65D 75/42 221/13 |
| 7,792,349 B2* | 9/2010 | Van Den Brink | G06K 9/00 382/140 |
| 7,963,201 B2* | 6/2011 | Willoughby | A61J 7/0084 117/106 |
| 8,019,417 B2 | 9/2011 | Bornzin et al. | |
| 8,086,350 B2* | 12/2011 | Timmermans et al. | 700/242 |
| 8,600,548 B2* | 12/2013 | Bossi et al. | 700/240 |
| 2002/0027507 A1 | 3/2002 | Yarin et al. | |
| 2002/0067270 A1 | 6/2002 | Yarin et al. | |
| 2003/0099158 A1 | 5/2003 | De la Huerga | |
| 2004/0117062 A1 | 6/2004 | Bonney et al. | |
| 2004/0158350 A1 | 8/2004 | Ostergaard et al. | |
| 2005/0041531 A1 | 2/2005 | Sekura | |
| 2005/0049747 A1* | 3/2005 | Willoughby | A61J 7/0084 700/232 |
| 2005/0240305 A1 | 10/2005 | Bogash et al. | |
| 2005/0268909 A1 | 12/2005 | Bonney et al. | |
| 2006/0071011 A1 | 4/2006 | Varvarelis et al. | |
| 2007/0043469 A1 | 2/2007 | Draper | |
| 2007/0185615 A1* | 8/2007 | Bossi et al. | 700/244 |
| 2007/0260487 A1 | 11/2007 | Bartfeld et al. | |
| 2008/0059228 A1 | 3/2008 | Bossi et al. | |
| 2008/0119958 A1 | 5/2008 | Bear et al. | |
| 2008/0215289 A1 | 9/2008 | Sekura | |
| 2008/0290106 A1* | 11/2008 | van der Klaauw et al. | 221/1 |
| 2009/0030730 A1 | 1/2009 | Dullemen et al. | |
| 2009/0084809 A1* | 4/2009 | Timmermans et al. | 221/1 |
| 2009/0198208 A1 | 8/2009 | Stavsky et al. | |
| 2010/0045466 A1 | 2/2010 | Sekura | |
| 2010/0127073 A1 | 5/2010 | van Esch | |
| 2010/0215231 A1 | 8/2010 | Bartfeld et al. | |
| 2010/0249997 A1 | 9/2010 | Greyshock et al. | |
| 2010/0305967 A1 | 12/2010 | Daya et al. | |
| 2011/0193705 A1 | 8/2011 | Sekura | |
| 2012/0004770 A1 | 1/2012 | Ooyen et al. | |
| 2012/0081225 A1* | 4/2012 | Waugh | A61J 7/0084 340/540 |
| 2012/0083666 A1 | 4/2012 | Waugh et al. | |
| 2012/0126958 A1 | 5/2012 | Kim et al. | |
| 2012/0199650 A1 | 8/2012 | Horst et al. | |
| 2012/0273087 A1 | 11/2012 | Stavsky et al. | |
| 2013/0169798 A1 | 7/2013 | Pellerin et al. | |
| 2014/0005826 A1* | 1/2014 | Apell et al. | 700/244 |

FOREIGN PATENT DOCUMENTS

| | | |
|---|---|---|
| WO | 91/04726 A1 | 4/1991 |
| WO | 00/07538 A2 | 2/2000 |
| WO | 01/47466 A1 | 7/2001 |
| WO | 02/078593 A2 | 10/2002 |
| WO | 03/001337 A2 | 1/2003 |
| WO | 2007/129318 A2 | 11/2007 |
| WO | 2008/135823 A1 | 11/2008 |
| WO | 2009/095904 A1 | 8/2009 |
| WO | 2011/042840 A1 | 4/2011 |
| WO | 2011/112606 A1 | 9/2011 |
| WO | 2011/123931 A1 | 10/2011 |
| WO | 2011/123933 A1 | 10/2011 |
| WO | 2012/007411 A1 | 1/2012 |

* cited by examiner

METHOD FOR MONITORING THE FILLING OF A MEDICATION DISPENSER, AND MEDICATION DISPENSER

TECHNICAL FIELD OF THE INVENTION

The present invention relates to a method for monitoring the filling of a medication dispenser and to a medication dispenser according to the preambles of the appended independent claims.

BACKGROUND OF THE INVENTION

A patient must usually take one or more medications in prescribed dosages and at certain time intervals. Various devices are known for assisting the patient in complying with his/her medical regimen. The most sophisticated devices are so-called medication dispensers, which dispense prepackaged and labelled medication packages to provide the patient with the proper dosage of medications at a prescribed time. The medications are prepackaged into packages according to the medical regimen of the patient, and are available from licensed pharmacies. The labels of the medication packages may contain information about the patient, the content of the package, and the date and time of the dosage.

Typically, the medication packages are arranged as a strip, which is inserted into a container of the medication dispenser either by the patient or a caregiver of the patient. The medication dispenser dispenses the packages by separating the packages from the strip one package at a time according to the information provided by the labels of the packages, or information stored in the medication dispenser. The medication dispenser allows the dispensation of medications to be monitored and controlled so that the patient, the caregiver or any other person having access to the apparatus can be assured that the patient is taking the medications as prescribed.

A problem associated with known medication dispensers, which dispense medication packages from a strip, relates to the filling of the dispensers. Because the dispensers are filled manually by a patient or a caregiver, there is always a risk of inserting a wrong strip into the medication dispenser, or a risk of inserting the strip into the medication dispenser in a wrong way. The known medication dispensers either do not have any functionality or are provided with insufficient means to ensure that the medication dispenser is filled correctly.

OBJECTIVES OF THE INVENTION

It is the main objective of the present invention to reduce or even eliminate prior art problems presented above.

It is an objective of the present invention to provide a method for monitoring the filling of a medication dispenser with a strip of medication packages. It is also an objective of the invention to provide a medication dispenser enabling to monitor the filling of the dispenser. In more detail, it is an objective of the invention to provide a method and a medication dispenser enabling to check and confirm that the right medication strip is inserted into the medication dispenser.

In order to realise the above-mentioned objectives, the method and the medication dispenser according to the invention are characterised by what is presented in the characterising parts of the appended independent claims. Advantageous embodiments of the invention are described in the dependent claims.

DESCRIPTION OF THE INVENTION

A typical method according to the invention for monitoring the filling of a medication dispenser comprises inserting a second strip of medication packages into a second container of the medication dispenser, transferring the first medication package of the second strip to a reader of the medication dispenser, and reading a taking time of the first medication package from a label of the first medication package. A typical method according to the invention further comprises comparing the taking time of the first medication package of the second strip with a taking time of the last medication package of a first strip inserted into a first container of the medication dispenser, in order to determine if the delivery of medication packages can be continued after the first strip with the second strip.

In a method according to the invention the first strip of medication packages has been inserted into the first container before the second strip of medication packages is inserted into the second container. The second strip may be inserted into the second container right after the first strip has been inserted into the first container, or after one or more of the medication packages from the first strip have been delivered to a patient. Preferably, the second strip is inserted into the second container before the last medication package of the first strip has been delivered to the patient.

The steps of a method according to the invention are preferably carried out during the filling phase so that the person filling the medication dispenser can immediately obtain information whether the inserted strip is right or wrong. In other words, once the second strip has been inserted into the second container, the steps of transferring, reading and comparing are performed without any unnecessary delays. For example, one or more of the steps are not delayed until the last medication package of the first strip has been delivered to the patient. The status of the filling process may be communicated in real-time to the person, for example, using a display.

The method according to the invention is based on comparing the taking times of the medication packages of two medication strips. By comparing the taking time of the first medication package of a strip inserted into the medication dispenser with the taking time of the last medication package of another strip that has been inserted earlier to the medication dispenser, it can be determined if the delivery of medication packages can be continued with the later inserted strip.

By a taking time of a medication package is meant a time at which the medications contained in the medication package should be taken by the patient.

The taking time of the last medication package of the first strip can be obtained in different ways. Preferably, the taking time of the last medication package of the first strip is inputted by the person who inserted the first strip into the first container. The taking time of the last medication package may be obtained from a patient's medical regimen that has been stored in the medication dispenser. The dispenser may also have a reader arranged to read the last medication package in the first strip during the refilling. In all of these cases, the taking time of the last medication package is available at a time when the second strip is inserted into the second container. In some cases the taking time of the last medication package is unknown until the label of the last medication package of the first strip is actually read.

If the taking time of the first medication package of the second strip is too early or too late compared to the taking time of the last medication package of the first strip, the second strip is wrong and thus may not be dispensed to the patient. A time window, within which the taking time of the first medication package should be to allow the medication packages of the second strip to be dispensed, can vary. The time differences between the taking time of the last medication package and the starting and the ending times of the time window can be constant for different strips. However, these time differences typically change, if the medical regimen of the patient is changed. Preferably, the time difference between the starting time of the time window and the taking time of the last medication package of the first strip is set zero, so that the starting time corresponds to the taking time of the last medication package.

There are several mechanisms that can be taken advantage of to define if the taking time of the first medication package of the second strip is too early or too late compared to the taking time of the last medication package of the first strip. First of all, the taking time of the first medication package of the second strip must not be earlier than the taking time of the last medication package of the first strip. The maximum time difference that is allowed between the last medication package of the first strip and the first medication package of the second strip can be constant, for example 8 hours, 1 day or 3 days. The maximum time difference can also be proportional to the medication history data. Then, the maximum time difference is automatically adjusted by the history data of the medical regimen of the patient. For example, if the patient has taken his/her medications within the maximum 8 hours, the medication dispenser automatically sets the maximum time difference to 8 hours. If the time is longer, the medication dispenser requires the person filling the dispenser to check and confirm the longer maximum time difference. The change may be caused for example by the change of the medical regimen.

The method according to the invention is intended to be used in a medication dispenser that comprises at least two containers for receiving a strip of medication packages. The strip comprises one or more medication packages. The strip may comprise, for example, at least two medication packages, or the strip may consist of one medication package. The strip may be inserted into the container by the patient or a caregiver of the patient, such as a nurse or a near relative. The medication packages are arranged in the strip sequentially in time order. The packages of the strip are meant to be dispensed one package at a time according to the medical regimen. Each package contains a dosage to be taken at a prescribed time. The packages can be, for example, bags or mugs made of plastic, or blister packages made of plastic or metal foil.

Typically each medication package of a strip has a label which contains package-related information, such as a taking time of the medication package. The label may also contain identification information of the person to whom the packages are meant to be dispensed, such as his/her name, date of birth or social security number, and/or information related to the medical regimen of the person, such as the content of the package. The information may be, for example, in a form of text, a one- or two-dimensional bar code, an RFID (radio frequency identification) or an NFC (near field communication) tag, or a magnetic tag.

The first package of the strip may be transferred to the reader either manually by the patient or the caregiver, or automatically by transfer means of the medication dispenser. The transfer means are arranged to transfer medication packages from the containers through the reader to an outlet of the medication dispenser. After the first medication package has been moved to the reader, the information on the label of the first package is read.

According to an embodiment of the invention the method comprises comparing the taking time of the first medication package of the second strip with the current time, in order to determine if the packages of the strip can be dispensed to the patient. If the time at which the first medication package of the second strip should be dispensed is earlier than the current time or too late compared to the current time, the dispensation of the strip is not allowed. The taking time of the first medication package of the second strip may also be compared to the dispensing history of the first strip. Medications are typically given at fixed times daily. If the medical regimen of the patient has not been changed, medication dispensation should continue following the same fixed times.

According to an embodiment of the invention the method comprises receiving the taking time of the last medication package of the first strip via a user interface of the medication dispenser. The user interface may comprise a display and a keyboard, or a touch screen display for inputting the taking time. The taking time of the last medication package is preferably received at a time when the first strip is inserted into the first container.

According to an embodiment of the invention the method comprises reading identification and/or medical information from the label of the first medication package of the second strip, and comparing said information with patient information stored in the medication dispenser, in order to determine if the second strip is correct for the patient.

Whether the second strip that has been inserted into the medication dispenser is correct or not for the patient is determined by comparing the identification and/or the medical information read from the label of the first medication package with the patient information stored in the medication dispenser. The determination of whether the second strip may be dispensed to the patient or not may be based on comparing one or more attributes of identification information and/or medical regimen. For example, the determination may be based on the name and the date of birth of the patient; if the name and the date of birth read from the label are the same as the name and the date of birth of the patient, the strip is considered to belong to the patient and thus may be dispensed.

The patient information stored in the medication dispenser contains identification information of the patient, such as his/her name, date of birth, or social security number. The identification information may also contain other identification codes of the patient, such as care unit specific codes, or other similar information. The patient information also contains information related to the medical regimen of the patient, such as information about medications, their dosages and the time of the dosages, i.e. taking times. The patient information that is stored in the medication dispenser concerns the patient, i.e. the person to whom the medication dispenser is intended to dispense medications. The patient information is stored in a memory of the medication dispenser. The patient information can be loaded into the memory and updated locally or from a server over a communications network. It is also possible to change the patient information completely for example in cases where the medication dispenser is given to another patient. In some cases the comparison of the information can be made at least partly on an external server.

If the identification information read from the label of the first medication package corresponds to the patient information stored in the medication dispenser, the second strip is right for the patient, and thus the medication dispenser is allowed to dispense the medication packages of the second strip. If the information read from the label of the first medication package differs from the patient information stored in the medication dispenser, the second strip is wrong for the patient, and thus the medication dispenser is prevented from dispensing the medication packages from the second strip.

If the medical information of the first package of the second strip differs from the medical regimen information of the patient, the strip is wrong for the patient, and thus the medication dispenser is prevented from dispensing the packages of the strip. However, if the medical information of the first package corresponds to the medical regimen information of the patient, the strip is right for the patient, and thus the packages of the strip may be dispensed to the patient.

An advantage of comparing the identification information and/or the medical information of the first medication package with the patient information stored in the medication dispenser is that it can be ensured that the patient receives his/her own medications.

According to an embodiment of the invention the method comprises notifying the person filling the medication dispenser if the medication dispenser is wrongly filled. In other words, the person filling the medication dispenser is notified if the medication dispenser is prevented from dispensing the medication packages of the strip. The medication dispenser may communicate the status of a filling process on a display, thus giving the person filling the dispenser an immediate feedback. The person filling the medication dispenser may be the patient, a caregiver of the patient or any other authorised person. The person filling the medication dispenser may also be notified in a case where the filling of the medication dispenser has been successful, i.e. where the medication dispenser is correctly filled.

According to an embodiment of the invention the person filling the medication dispenser is notified with an audio or visual signal so as to draw the attention of the person to the fact that the strip is not correct. The person may be notified with an alarm that is played using a loudspeaker. The person may be notified visually using a lamp or a display.

According to an embodiment of the invention the caregiver is notified with a message sent over a communications network to a mobile device. The message can be, for example, an SMS (short message service) or MMS (multimedia messaging service) message, or a voice call. In addition to notifying the caregiver of the wrong strip, the message may contain information about the patient, and the time at which the patient should take the next medications. The caregiver may also be notified when the medication dispenser has been filled with a right strip. It is also possible to notify the caregiver in a case where the patient has not taken the medications.

According to an embodiment of the invention the method comprises sending a message over a communications network to a server if the medication dispenser is wrongly filled.

According to an embodiment of the invention the step of reading the taking time or the identification and/or medical information from the label of the first medication package of the second strip comprises capturing an image of the label, and interpreting the image using optical character recognition and/or bar code recognition.

In addition to reading the information from a label of a medication package, the reader may also be used for detecting the presence of a label and/or the position of a medication package. According to an embodiment of the invention the method comprises detecting the presence of the label of the first medication package. If the first medication package has been transferred to the reader, but the label of the first medication package cannot be detected, the strip is not correctly inserted into the container. A probable reason for not detecting the label is that the wrong side of the medication package is facing the reader. Another probable reason is that the first medication package is empty and there is no label at all in the first medication package. Then, the empty medication package of the strip should be removed before the filling.

It may also happen that the strip is inserted into the container in a wrong way so that the first medication package of the strip that is transferred to the reader is the package that is meant to be dispensed last. According to an embodiment of the invention the method comprises determining if the first medication package of the strip is the package that is meant to be dispensed first. If the first medication package is the package that is meant to be dispensed last, then the dispensation is prevented.

According to an embodiment of the invention the method comprises reading information from a label of the first medication package in the first container before and after the second strip is inserted into the second container, and comparing said information, in order to ensure that the first strip is still the same. A strip can be changed accidentally or by purpose. The medication dispenser can detect the presence of the first strip and read the information of the first medication package of the first strip. After filling, the first medication package of the first strip is re-read to check that the first strip has not been accidentally changed. If a change is detected and it has been done by purpose, the change has to be confirmed. Filling can be restarted and corrected if the change has been done accidentally.

The invention also relates to a medication dispenser. A typical medication dispenser according to the invention comprises a first container arranged to receive a first strip of medication packages, a second container arranged to receive a second strip of medication packages, a reader arranged to read a taking time of a medication package from a label of the medication package, transfer means for transferring medication packages from the first and the second container to the reader and then to an outlet of the medication dispenser, and a control unit arranged to control the reader and the transfer means. In a typical medication dispenser according to the invention the control unit is arranged to compare a taking time of the first medication package of the second strip with a taking time of the last medication package of the first strip, in order to determine if the delivery of medication packages can be continued after the first strip with the second strip.

The medication dispenser is arranged to dispense medication packages to provide the patient with the proper dosage of medications at a prescribed time. The time at which a medication package is to be delivered to the patient, i.e. a taking time, is read either from a label of the medication package or from a memory of the medication dispenser. The medication dispenser allows the dispensation of medications to be monitored and controlled so that the patient, a caregiver of the patient or any other person having access to the medication dispenser can be assured that the patient is taking the medications as prescribed.

The control unit is connected to the reader and the transfer means, and arranged to control the reader and the transfer means so that one medication package is dispensed at a time at determined times. The medication packages are transferred with the transfer means from the first or the second container to the reader and further to the outlet of the medication dispenser, from which outlet the patient can take the medications. The transfer means may comprise for example one or more rollers, which are driven by means of an electric motor. The electric motor is controlled by the control unit. The control unit comprises a processor that is programmed to carry out the functions that are needed to operate the medication dispenser. The control unit also comprises a memory for storing, for example, the patient information.

The medication package to be dispensed may be separated from the strip by a cutter and then transferred to the outlet. The cutter may also be arranged to open the medication package, whereby the medications can easily be taken out of the package. In some applications, the cutter is only arranged to cut open the medication package without separating the package from the strip. In this case, only the medications are delivered to the outlet. The outlet is preferably provided with a lid that may be lockable so that the access of the patient to the outlet can be prevented if desired.

The medication dispenser according to the invention comprises at least two containers from which medication packages can be dispensed to a patient. The number of containers can be, for example, 2, 3-5 or 5-10. The medication dispenser is preferably arranged to dispense medication packages from one container at a time. In other words, medication packages are dispensed from one container until it is empty and then the dispensation is continued from another container. This arrangement provides a longer time period between the fillings. Even though the medication packages are typically dispensed from one container at a time, it may be possible to dispense medication packages from two or more containers in turn or in other determined order. The reader is arranged to be moveable with respect to the containers so that the reader can read information from labels of medication packages of different strips.

According to an embodiment of the invention the medication dispenser comprises a user interface arranged to receive the taking time of the last medication package of the first strip. The user interface is communicatively connected to the control unit so that data may be transferred between the control unit and the user interface. The user interface may comprise a display and a keyboard, or a touch screen display.

According to an embodiment of the invention the reader is arranged to read identification and/or medical information from the label of the first medication package of the second strip, and the control unit is arranged to compare the identification and/or medical information with patient information stored in the medication dispenser, in order to determine if the second strip is correct for the patient.

According to an embodiment of the invention the reader is an optical reader, an RFID reader or an NFC reader. The optical reader may be capable of reading text or a one- or two-dimensional bar code. The RFID and NFC readers are used to read RFID and NFC tags, respectively. The reader may also be based on the use of a so-called Hall sensor.

According to an embodiment of the invention the reader comprises a camera arranged to capture an image of the label, and the control unit is arranged to interpret the image using optical character recognition and/or bar code recognition.

According to an embodiment of the invention the control unit is arranged to notify the person filling the medication dispenser if the medication dispenser is wrongly filled. In other words, the person is notified in a case where the strip arranged into the container is not allowed to be dispensed. The control unit may be arranged to notify the person by means of a loudspeaker, a light source, such as a LED, or a display.

According to an embodiment of the invention the control unit is arranged to send a message over a communications network to a mobile device.

According to an embodiment of the invention the control unit is arranged to send a message over a communications network to a server if the medication dispenser is wrongly filled.

According to an embodiment of the invention the medication dispenser comprises a detector arranged to detect the presence of a strip in the container. When inserting the strip, the strip is detected by means of the detector. The detector produces a signal according to which the control unit controls the transfer means to transfer the first package of the strip to the reader.

The method and the medication dispenser according to the invention provide a way to ensure that the medication dispenser is filled with a correct strip of medication packages. With the present invention it can be ensured that a medication strip inserted into a container of the medication dispenser is timely correct compared to an earlier strip inserted into another container of the medication dispenser.

The exemplary embodiments of the invention presented in this text are not interpreted to pose limitations to the applicability of the appended claims. The verb "to comprise" is used in this text as an open limitation that does not exclude the existence of also unrecited features. The features recited in the dependent claims are mutually freely combinable unless otherwise explicitly stated.

The exemplary embodiments presented in this text and their advantages relate by applicable parts to the method as well as the medication dispenser according to the invention, even though this is not always separately mentioned.

BRIEF DESCRIPTION OF THE DRAWINGS

The novel features which are considered as characteristic of the invention are set forth in particular in the appended claims. The invention itself, however, both as to its construction and its method of operation, together with additional objects and advantages thereof, will be best understood from the description of specific embodiments when read in connection with the accompanying drawings.

DETAILED DESCRIPTION OF THE DRAWINGS

Figure 1:
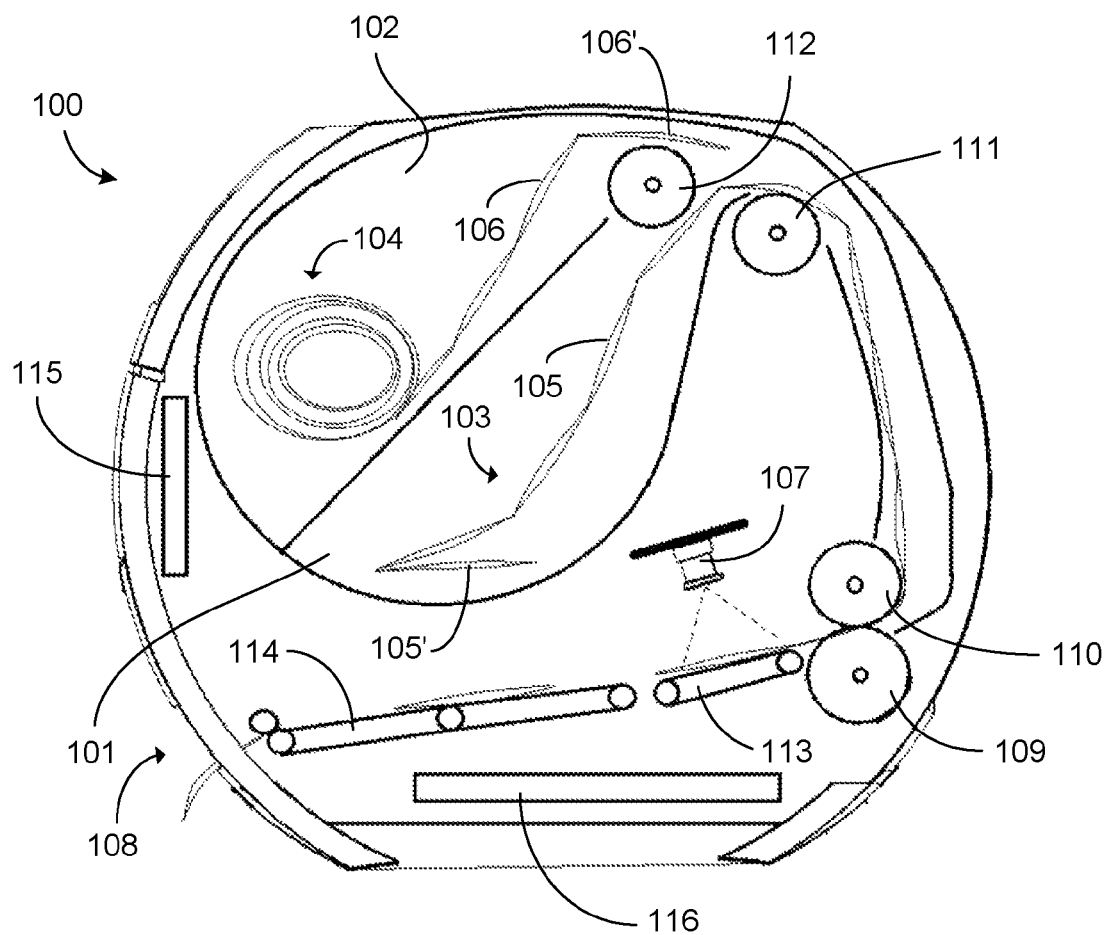
FIG. 1 illustrates a medication dispenser according to an embodiment of the invention.

FIG. 1 illustrates a medication dispenser according to an embodiment of the invention. The medication dispenser 100 comprises two containers 101, 102, into which strips 103, 104 that contain medication packages 105, 105', 106, 106' have been inserted. The medication packages 105, 105', 106, 106' have labels, which can be read with a reader 107.

In the situation that is shown in FIG. 1, the medications are delivered to a patient from the strip 103 that has been inserted into the container 101. After the medication packages 105, 105' of the strip 103 have been dispensed, the delivery of medications is continued with the strip 104 that has been inserted into the container 102. The correctness of the strip 104 has been ensured at the filling phase by comparing the taking time of the first medication package 106' of the strip 104 with the taking time of the last medication package 105' of the strip 103.

The medication dispenser 100 comprises transfer means for transferring the medication packages 105, 105', 106, 106' from the containers 101, 102 to the reader 107 and then to an outlet 108 of the medication dispenser 100. The transfer means comprise rollers 109, 110, 111, 112 for transferring the strips 103, 104 from the containers 101, 102 to the reader 107, and roller tables 113, 114 for transferring the separated medication packages 105, 105', 106, 106' from the reader 107 to the outlet 108.

The communication between the patient and the medication dispenser 100 is performed with a touch screen display 115 that is controlled by a control unit 116. The control unit 116 also controls the reader 107 and the transfer means.

The medication dispenser 100 of FIG. 1 comprises a camera as the reader 107. The camera is arranged to capture an image of a label of a medication package that has been transferred on the roller table 113. The control unit 116 is arranged to interpret the image using optical character recognition and/or bar code recognition and to compare the information read from the label with the taking time, and/or the patient information stored in the medication dispenser 100.

Figure 2:
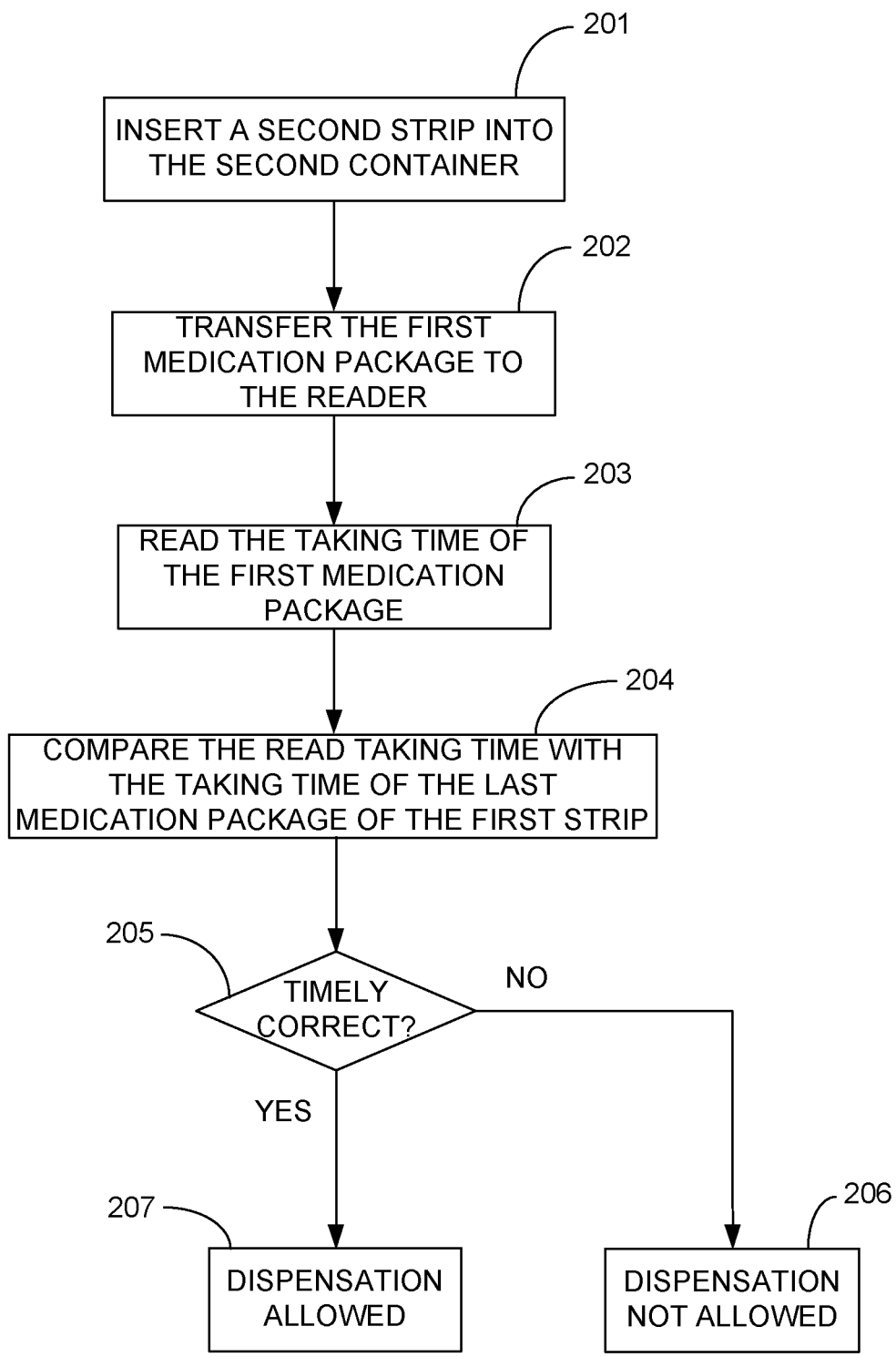
FIG. 2 illustrates a flow diagram of a method according to an embodiment of the invention.

FIG. 2 illustrates a flow diagram of a method according to an embodiment of the invention. The method is meant for monitoring the filling of a medication dispenser 100.

At step 201 a second strip 104 containing medication packages 106, 106' is inserted into a second container 102 of the medication dispenser 100. Each medication package 106, 106' has a label that contains information relating to the package, such as a taking time. The second strip 104 may be inserted into the second container 102 by the patient or the caregiver.

At step 202 the first medication package 106' of the second strip 104 is transferred to a reader 107 of the medication dispenser 100. The first medication package 106' of the second strip 104 may be transferred to the reader 107 either manually by the patient or the caregiver, or automatically by transfer means of the medication dispenser 100. The transfer means are arranged to transfer medication packages 105, 105', 106, 106' from the containers 101, 102 through the reader 107 to an outlet 108 of the medication dispenser 100. At step 203 a taking time of the first medication package 106' is read from the label with the reader 107.

At step 204 the taking time of the first medication package 106' of the second strip 104 is compared with a taking time of the last medication package 105' of a first strip 103 inserted into a first container 101 of the medication dispenser, in order to determine if the delivery of medication packages can be continued after the first strip 103 with the second strip 104. The determination is done at step 205.

If the taking time of the first medication package 106' of the second strip 104 is too early or too late compared to the taking time of the last medication package 105' of the first strip 103, the dispensation of the medication packages 106, 106' of the second strip 104 is not allowed (step 206). Otherwise, the dispensation is allowed (step 207).

Only advantageous exemplary embodiments of the invention are described in the figures. It is clear to a person skilled in the art that the invention is not restricted only to the examples presented above, but the invention may vary within the limits of the claims presented hereafter. Some possible embodiments of the invention are described in the dependent claims, and they are not to be considered to restrict the scope of protection of the invention as such.

The invention claimed is:

1. A method for monitoring the filling of a medication dispenser, comprising:
   inserting a second strip of medication packages into a second container of the medication dispenser by a person;
   transferring a first medication package of the second strip to a reader of the medication dispenser during a filling phase of the medication dispenser;
   reading a taking time of the first medication package of the second strip from a label of the first medication package of the second strip during the filling phase;
   comparing the taking time of the first medication package of the second strip with a taking time of a last medication package of a first strip inserted into a first container of the medication dispenser during the filling phase, in order to immediately determine if the delivery of medication packages can be continued after the first strip with the second strip and that the medication dispenser has been correctly filled;
   each of the first and second strips comprising at least two medication packages, and sequentially arranging the at least two medication packages in the first and second strips in time order; and
   performing the transferring of the first medication package of the second strip to the reader of the medication dispenser, the reading of the taking time of the first medication package of the second strip from the label of the first medication package of the second strip, and the comparing of the taking time of the first medication package of the second strip with the taking time of the last medication package of the first strip immediately once the second strip has been inserted into the second container, and wherein the steps of the transferring, the reading, and the comparing of the taking time of the first medication package of the second strip with the taking time of the last medication package of the first strip are not delayed until the last medication package of the first strip has been delivered to a patient.

2. The method according to claim 1, wherein the method comprises:
   receiving the taking time of the last medication package of the first strip via a user interface of the medication dispenser.

3. The method according to claim 1, wherein the method comprises:
   reading identification and/or medical information from the label of the first medication package of the second strip, and
   comparing said information with patient information stored in the medication dispenser, in order to determine if the second strip is correct for the patient.

4. The method according to claim 1, wherein the method comprises:
   notifying the person filling the medication dispenser if the medication dispenser is wrongly filled.

5. The method according to claim 4, wherein the person filling the medication dispenser is notified with an audio or visual signal.

6. The method according to claim 1, wherein the method comprises:
sending a message over a communications network to a server if the medication dispenser is wrongly filled.

7. The method according to claim 1, wherein the step of reading the taking time or the identification and/or medical information from the label of the first medication package of the second strip comprises:
capturing an image of the label, and
interpreting the image using optical character recognition and/or bar code recognition.

8. The method according to claim 1, comprising:
separating the at least two medication packages in the first and second strips from an adjacent medication package when dispensing a medication package from the medication dispenser.

9. The method according to claim 1, wherein the filling phase of the medication dispenser comprises:
manually inserting the medication packages of the first strip and the medication packages of the second strip into the medication dispenser.

10. A medication dispenser, comprising:
a first container arranged to receive a first strip of medication packages;
a second container arranged to receive a second strip of medication packages;
a reader arranged to read a taking time of a medication package from a label of the medication package;
transfer means for transferring medication packages from the first and the second container to the reader and then to an outlet of the medication dispenser;
a control unit arranged to control the reader and the transfer means,
wherein the control unit is arranged to compare a taking time of the first medication package of the second strip with a taking time of the last medication package of the first strip during a filling phase of the medication dispenser, in order to immediately determine if the delivery of medication packages can be continued after the first strip with the second strip and that the medication dispenser has been correctly filled;
each of the first and second strips comprises at least two medication packages, and wherein the at least two medication packages in the first and second strips are sequentially arranged in time order; and
wherein the transferring of the first medication package of the second strip to the reader of the medication dispenser, the reading of the taking time of the first medication package of the second strip from the label of the first medication package of the second strip, and the comparing of the taking time of the first medication package of the second strip with the taking time of the last medication package of the first strip is performed immediately once the second strip has been inserted into the second container, and wherein the transferring, the reading, and the comparing of the taking time of the first medication package of the second strip with the taking time of the last medication package of the first strip are not delayed until the last medication package of the first strip has been delivered to a patient.

11. The medication dispenser according to claim 10, wherein the medication dispenser comprises a user interface arranged to receive the taking time of the last medication package of the first strip.

12. The medication dispenser according to claim 10, wherein:
the reader is arranged to read identification and/or medical information from the label of the first medication package of the second strip, and
the control unit is arranged to compare the identification and/or medical information with patient information stored in the medication dispenser, in order to determine if the second strip is correct for the patient.

13. The medication dispenser according to claim 10, wherein the reader is an optical reader, an RFID reader or an NFC reader.

14. The medication dispenser according to claim 10, wherein the reader comprises a camera arranged to capture an image of the label, and the control unit is arranged to interpret the image using optical character recognition and/or bar code recognition.

15. The medication dispenser according to claim 10, wherein the control unit is arranged to notify a person filling the medication dispenser if the medication dispenser is wrongly filled.

16. The medication dispenser according to claim 10, wherein the control unit is arranged to send a message over a communications network to a server if the medication dispenser is wrongly filled.

17. The medication dispenser according to claim 10, wherein the medication dispenser comprises a detector arranged to detect the presence of a strip in the container.

18. The medication dispenser according to claim 10, wherein the at least two medication packages in the first and second strips are separated from an adjacent medication package when a medication package is dispensed from the medication dispenser.

* * * * *